United States Patent [19]
Nagaoka

[11] Patent Number: 6,090,615
[45] Date of Patent: Jul. 18, 2000

[54] METHOD FOR EXTRACTING A BASIDIOMYCETES MYCELIUM-CONTAINING CULTURE MEDIUM USING β-1,3-GLUCANASE

[76] Inventor: Hitoshi Nagaoka, 2-22-13, Kotobuki, Abiko-shi, Chiba 270-11, Japan

[21] Appl. No.: 08/779,946

[22] Filed: Dec. 23, 1996

[30] Foreign Application Priority Data

Dec. 25, 1995 [JP] Japan ................................ 7-337557
Dec. 25, 1995 [JP] Japan ................................ 7-337558

[51] Int. Cl.[7] ........................... C02F 1/00; C07G 17/00; C12N 1/06; C12P 1/00
[52] U.S. Cl. ........................... 435/267; 210/632; 435/41; 435/259
[58] Field of Search ........................... 435/184, 41, 259, 435/267; 210/632

[56] References Cited

U.S. PATENT DOCUMENTS

| | | | |
|---|---|---|---|
| 4,178,210 | 12/1979 | Demain et al. | 435/47 |
| 5,756,318 | 5/1998 | Kosuna | 435/101 |

FOREIGN PATENT DOCUMENTS

| | | |
|---|---|---|
| 54-46859 | 4/1979 | Japan . |
| 58-107159 | 6/1983 | Japan . |
| 60-149369 | 8/1985 | Japan . |
| 60-149528 | 8/1985 | Japan . |
| 63-202356 | 8/1988 | Japan . |
| 9212418 | 7/1992 | Rep. of Korea . |

OTHER PUBLICATIONS

Oka, Sutemi et al., *Antitumor Activity of Some Plant Polysaccharides, Gann*, vol. 59, pp. 35–42, Feb. 1968.
Japanese Article (Untranslated) from *New Food Industry*, vol. 8 (1986), pp. 17–21.

*Primary Examiner*—David M. Naff
*Assistant Examiner*—Deborah K. Ware
*Attorney, Agent, or Firm*—Webb Ziesenheim Lodgson Orkin & Hanson, P.C.

[57] ABSTRACT

Useful ingredients are extracted from a mycelium-containing culture medium by the steps of inoculating basidiomycetes in a solid culture medium containing bagasse as a substrate and proliferating mycelium, and then squeezing the solid culture medium containing proliferated mycelium to obtain a squeeze liquid (i), separately, adding water and beta 1,3, glucanase and at least one enzyme selected from the group consisting of chitinase, cellulase and protease to a mycelium-containing solid residue having been separated from the squeeze liquid (i), stirring the resulting mixture with maintaining the mixture at 30 to 60°0 C. to lyse mycelial cell walls, and heating the resulting cell wall lysis product-containing liquid (ii) up to a temperature of 95° C. to inactivate the enzyme and perform sterilization. The cell wall lysis product-containing liquid (ii) contains β-glucan in a high concentration and shows excellent antitumor effects. The obtained squeeze liquid (i) contains cytokinin-like substances in high concentrations together with metabolites of the mycelium, and this liquid is clear; therefore, application of this liquid to tonic drinks, plant hormone drugs and cosmetic materials can be expected.

7 Claims, No Drawings

METHOD FOR EXTRACTING A BASIDIOMYCETES MYCELIUM-CONTAINING CULTURE MEDIUM USING β-1,3-GLUCANASE

FIELD OF THE INVENTION

The present invention relates to methods for extracting useful ingredients from mycelium-containing culture media, and more particularly to methods for extracting useful ingredients from mycelium-containing culture media, which enable obtaining useful ingredients of basidiomycetous mycelia and those of their culture media in high yields for a short period of time.

BACKGROUND OF THE INVENTION

From ancient times, mushrooms of basidiomycetes, such as *Lentinus edodes, Trichloma matsutake* and *Flammulina velutipes,* have been used for foods, and some of them, e.g., Polyporaceae of basidiomycetes, have been valuably used as Chinese medicines.

Meanwhile, various methods to extract active ingredients from the basidiomycetes have been proposed. For example, Japanese Patent Laid-Open Publication No. 46859/1979 discloses a method for preparing a healthful food comprising the steps of inoculating basidiomycetes in a culture medium mainly composed of bagasse, proliferating the mycelium and squeezing the culture medium containing proliferated mycelium to obtain active ingredients.

The effect of the bagasse of the culture medium used in this method is described in, for example, a monograph by Sutemi Oka, et al., "ANTITUMOR ACTIVITY OF SOME PLANT POLYSACCHARIDES (FRACTIONATION AND ANTITUMOR ACTIVITY OF BAGASSE POLYSACCHARIDE)", GANN, Vol. 59, pp. 35 to 42, February, 1968. In more detail, it is described that a fraction obtained from a crude powder of bagasse polysaccharide contains galactose, arabinose, xylose and mannose along with a small amount of glucose and intraperitoneal injections of the fraction resulted in remarkable inhibitory effect on the growth of subcutaneously implanted Sarcoma 180 (kind of sarcoma, malignant tumor) in mice. Therefore, health effects given by intake of ingredients of the bagasse can be expected.

In the method described in the above publication, however, there is a problem in that the extraction efficiency is bad because concentrations of the active ingredients in the separate liquid are low and hence a complicated concentrating operation is necessary.

The present inventors have studied to solve such a problem as mentioned above and proposed, in Japanese Patent Application No. 34123/1987, "a method for extracting useful ingredients from *Flammulina velutipes* mycelium and a bagasse culture medium, comprising the steps of inoculating *Flammulina velutipes* fungus in a solid culture medium containing bagasse as a substrate, then disentangling the solid culture medium containing proliferated mycelium in such a manner that the amount of the 12-mesh passing disentangled culture medium becomes not more than 30 w/w %, adding water and at least one enzyme selected from the group consisting of cellulase, protease and glucosidase to the disentangled solid culture medium, crushing and grinding the solid culture medium in the presence of the enzyme so that the amount of the 12-mesh passing bagasse fibers becomes at least 70 w/w %, then heating up to a temperature of 95° C. to inactivate the enzyme and perform sterilization".

The present inventors have further proposed, in Japanese Patent Publication No. 23826/1985, a method for preparing a healthful drink comprising the same steps as in the method of Japanese Patent Application No. 34123/1987 except that *Lentinus edodes* fungus is used as the fungus to be inoculated.

The present inventors have furthermore proposed a method for preparing a healthful drink using *Ganoderuma lucidium* fungus in Japanese Patent Application No. 5355/1984 (Japanese Patent Publication No. 35149/1992) and Japanese Patent Application No. 5356/1984 (Japanese Patent Publication No. 6171/1992).

According to the methods proposed by the present inventors, useful ingredients can be extracted in high concentrations from the mycelia (*Flammulina velutipes* mycelium, *Lentinus edodes* mycelium and *Ganoderuma lucidium* mycelium) and the bagasse culture media.

In these methods, however, repeated heat treatments are generally carried out from the viewpoint of extraction efficiency. For example, the crushing-grinding operation of the solid culture medium having been added with an enzyme is carried out under heating at a temperature of usually 30 to 50° C., the inactivation of enzyme is carried out under heating at a temperature of up to 95° C., and also the sterilization is carried out under heating.

The present inventors have earnestly studied to further improve the extraction efficiency, and they have found that useful ingredients such as β-glucan can be efficiently extracted from basidiomycetous mycelium and a bagasse solid culture medium by:

a method comprising the steps of squeezing a bagasse culture medium containing proliferated basidiomycetous mycelium to separate it into a solid component containing mycelium and a squeeze liquid and subjecting the mycelium-containing solid component to a specific treatment, or a method comprising the steps of disentangling a bagasse culture medium containing proliferated basidiomycetous mycelium, contacting the mycelium-containing bagasse culture medium with a specific enzyme (i.e., allowing a specific enzyme to act on the culture medium) under specific conditions and heating the resulting cell wall lysis product-containing liquid to inactivate the enzyme and perform sterilization.

Based on the finding, the present invention has been accomplished.

In a monograph entitled "On The New Cell Wall Lytic Enzymes" (by Shinichiro Shimada, New Food Industry, Vol. 28, No. 8 (1986)), it is described that mycelium obtained by complete culturing of each mushroom of *Pleurotus ostreatus* and *Flammulina velutipes* is treated with a 2% solution (pH: 5.6) of Fanselase (trade name of enzyme reagent, available from Yakult K.K.) under the temperature conditions of 30° C. for 1 or 2 hours to thereby produce protoplast. It is further described that protoplast is produced also from *Lentinus edodes* mycelium.

In the above monograph, however, there is not so much as suggestion on the methods to efficiently extract the useful ingredients such as β-glucan from the basidiomycetous mycelia and the bagasse culture media. Actually, even if the above mycelia are contacted with Fanselase under the above temperature conditions for a long period of time, the useful ingredients such as β-glucan having antitumor activity cannot be efficiently extracted from the basidiomycetous mycelia and the bagasse culture media.

SUMMARY OF THE INVENTION

The present invention has been made to solve such a problem associated with the prior art as described above, and it is an object of the invention to provide methods for extracting useful ingredients from a mycelium-containing culture medium, which enable obtaining useful ingredients of the mycelium and the culture medium in high yields for a short period of time.

The first method for extracting useful ingredients containing a squeeze liquid (i) and a cell wall lysis product-containing liquid (ii) from a mycelium-containing culture medium according to the present invention comprises the steps of:

inoculating basidiomycetes in a solid culture medium containing bagasse as a substrate and proliferating mycelium, and then squeezing the solid culture medium containing proliferated mycelium to obtain a squeeze liquid (i), separately, adding water and an enzyme (preferably enzymes containing a cell wall lytic enzyme) to a mycelium-containing solid residue (solid component) having been separated from the squeeze liquid (i), then stirring the resulting mixture while maintaining the mixture at 30 to 60° C. to lyse (decompose) mycelial cell walls, and heating the resulting cell wall lysis product-containing liquid (ii) up to a temperature of 95° C. to inactivate the enzyme and perform sterilization.

It is preferred that in the first method of the invention, after the cell wall lysis product-containing liquid has been previously subjected to solid-liquid separation, the resulting separate liquid (iii) is heated up to a temperature of 95° C. to inactivate the enzymes and perform sterilization.

The second method according to the present invention comprises the steps of:

inoculating basidiomycetes in a solid culture medium containing bagasse as a substrate and proliferating mycelium, and then squeezing the solid culture medium containing proliferated mycelium to obtain a squeeze liquid (i), separately, disentangling a mycelium-containing solid residue (solid component) having been separated from the squeeze liquid (i), adding water and an enzyme (preferably enzymes containing a cell wall lytic enzyme) to the disentangled solid residue (solid component), then crushing and grinding the solid component while maintaining the mixture at 30 to 60° C. to lyse mycelial cell walls, and heating the resulting cell wall lysis product-containing liquid (ii) up to a temperature of 95° C. to inactivate the enzyme and perform sterilization.

It is preferred that in the second method of the invention, after the cell wall lysis product-containing liquid has been previously subjected to solid-liquid separation, the resulting separate liquid (iii) is heated up to a temperature of 95° C. to inactivate the enzymes and perform sterilization.

The third method according to the present invention comprises the steps of:

inoculating basidiomycetes in a solid culture medium containing bagasse as a substrate and proliferating mycelium, and then disentangling the solid culture medium containing proliferated mycelium, contacting the disentangled solid culture medium with a β-1,3-glucanase-containing liquid (a) at a temperature of 30 to 60° C. for 1 to 65 minutes to lyse mycelial cell walls, and heating the resulting cell wall lysis product-containing liquid up to a temperature of 95° C. to inactivate the enzyme and perform sterilization.

In the third method, it is preferable that 100 to 2,000 ml of the enzyme liquid (a) having a concentration of 0.01 to 0.1 w/w % is allowed to act on 1 kg of the solid culture medium.

The contact of the solid culture medium with the enzyme liquid (a) is preferably carried out by immersing the disentangled solid culture medium in the enzyme liquid (a).

It is preferable that in the third method of the invention, after the cell wall lysis product-containing liquid has been previously subjected to solid-liquid separation, the resulting separate liquid is heated up to a temperature of 95° C. to inactivate the enzymes and perform sterilization.

In a preferred embodiment of each of the first and second methods, the enzyme contains β-1,3-glucanase and preferably contains β-1,3-glucanase and at least one kind selected from the group consisting of chitinase, cellulase and protease (e.g., liquid containing "Fanselase"). Also in the third method, it is desirable that the enzyme liquid (a) further contains at least one enzyme selected from the group consisting of chitinase and cellulase and protease in addition to β-1,3-glucanase.

In the methods according to the present invention, it is preferable to use either *Lentinus edodes, Flammulina velutipes, Ganoderuma lucidium* or *Grifola frondosa* as the basidiomycetes, and it is more preferable to use either *Ganoderuma lucidium* or *Grifola frondosa* as the basidiomycetes.

By any of the first to third methods of the invention, useful ingredients from the basidiomycetous mycelium-containing culture medium can be obtained in high yields in a short period of time.

According to the first and second methods, there can be obtained a cell wall lysis product-containing liquid (separate liquid) having excellent antitumor effects, in which β-glucan (i.e., cell wall decomposition product of basidiomycetes) having high antitumor effects and antiviral effects is contained in a high concentration. Further, these methods have an advantage that the heat treatment for inactivation of enzyme and sterilization is carried out only once in the final stage.

In the squeeze liquid obtained in the first and second methods, cytokinin-like substances having a function of imparting immunity and a hormonic action on plants are contained in high concentrations together with glucose which is a metabolite of the mycelium. Besides, this squeeze liquid is generally clear, so that application of the liquid to tonic drinks, plant hormone drugs and cosmetic materials can be expected.

In the cell wall lysis product-containing liquid (extract) obtained by the third method, β-glucan showing the above effects is contained in a high concentration. In this extract, further, cytokinin-like substances are contained in high concentrations together with glucose and these components are well-balanced, so that the above-mentioned use application can be expected.

DETAILED DESCRIPTION OF THE INVENTION

The methods for extracting useful ingredients from a mycelium-containing culture medium according to the invention will be described in detail hereinafter.

First and Second Methods

Culturing of mycelium

As a substrate of the solid culture medium for use in the invention, bagasse or a mixture of bagasse and rice bran is employable. The bagasse is a refuse product from sugar cane. In the bagasse, saccharides and proteins, which become nutritive resources of the mycelium, are contained, so that the bagasse is employable as it is as the solid culture medium. However, it is preferable to add 10 to 30 parts by weight of rice bran to bagasse based on 100 parts by weight of the bagasse, to prepare a solid culture medium.

In the solid culture medium containing bagasse as a substrate, spawn of basidiomycetes such as *Lentinus edodes* and *Flammulina velutipes* are inoculated. Then, the solid culture medium wherein the basidiomycetes have been inoculated is allowed to stand for a given period of time in a culture room under the adjusted temperature, humidity and illuminance, whereby the basidiomycetous mycelium is proliferated. Examples of the basidiomycetes include:

mushrooms of Agaricales, which are generally used for foods, such as *Trichloma matsutake, Lentinus edodes, Flammulina velutipes, Pleurotus ostreatus, Pholiota nameko,* Boletus, Lyophyllum and *Lactarius volemus;* mushrooms of Polyporales, which are used as Japanese and Chinese medicines or used for foods, such as *Fomes applanatus, Fomes piniocola, Coriolus versicolor, Ganoderuma lucidium* and *Grifola frondosa;* and mushrooms of Auriculariales and Tremellales, which are generally used for foods, such as Auricularia and Tremella.

Of these mushrooms of the basidiomycetes, preferably used are *Lentinus edodes, Flammulina velutipes, Pleurotus ostreatus, Grifola frondosa* and *Ganoderuma lucidium* from the viewpoints of ease of culturing, nutritive value and medicinal effects.

Squeezing

The basidiomycetous mycelium proliferates thoroughly in the culture medium as described above. Then, immediately before or after fructification, the resulting bagasse culture medium containing mycelium (sometimes referred to as "bagasse culture medium block" or "solid culture medium") is squeezed to separate the solid culture medium into a squeeze liquid (i) (primary extract) and a solid residue (i-a) containing mycelium (sometimes referred to as "solid component"), whereby the squeeze liquid (i) is obtained. The squeezing of the bagasse culture medium is preferably carried out immediately before or after the fructification as described above.

The squeezing operation is carried out generally at a pressure of 50 to 200 kg/cm$^2$ for about 1 to 10 minutes, preferably at a pressure of 80 to 180 kg/cm$^2$ for about 3 to 5 minutes. This squeezing operation may be conducted in one stage or may be conducted in plural stages under the same or different pressure conditions.

When the squeezing of the bagasse culture medium is carried out in two or more stages, the first squeezing operation may be done at a pressure of 50 to 100 kg/cm$^2$ for about 1 to 10 minutes, preferably at a pressure of 60 to 85 kg/cm$^2$ for about 3 to 5 minutes, and the second squeezing operation may be done at a pressure of 100 to 200 kg/cm$^2$ for about 1 to 10 minutes, preferably at a pressure of 150 to 180 kg/cm$^2$ for about 3 to 5 minutes.

If the squeezing operation is carried out in plural stages with stepwise increasing the pressure, or if the squeezing operation is carried out in one stage preferably with gradually increasing the pressure, the extraction of the liquid is not made locally only on the surface of the culture medium but made efficiently and almost uniformly from the whole culture medium.

In the solid residue (i-a) obtained by the above operation, the mycelial component of the *Lentinus edodes* is contained nearly as it is. In the squeeze liquid (i), further, cytokinin-like substances having a function of imparting immunity and a hormonic action on plants are contained in high concentrations together with glucose which is a metabolite of the mycelium. Moreover, the squeeze liquid (i) is generally clear, so that application of the liquid (i) to tonic drinks, plant hormone drugs and cosmetic materials can be expected.

In the squeeze liquid (i), autodigestive enzymes derived from the intracellular substances are also contained. When these enzymes are heated to be inactivated, they are generally thermally denatured and precipitated. The precipitate thus obtained may be subjected to amino acid decomposition by being acted on by proteolytic enzymes such as protease. Thus, the utility value of the squeeze liquid (i) is further increased.

Mycelial cytolysis in the solid component

To the mycelium-containing solid component (i-a) obtained above, water and an enzyme, preferably water and a mycelial cell wall lytic enzyme, are added. Then, the resulting mixture is stirred while maintaining the mixture at 30 to 60° C., preferably 30 to 55° C., to lyse the mycelial cell walls. The stirring is carried out for usually 10 to 60 minutes, preferably 15 to 30 minutes. The amount of water can be optionally determined.

In the present invention, the mycelium-containing solid component (i-a) may be disentangled, then to the disentangled solid component are added water and an enzyme, preferably water and a mycelial cell wall lytic enzyme (cell wall lytic enzyme), and the solid component is crushed and ground while maintaining the mixture at the above-mentioned temperature to lyse the mycelial cell walls. The disentangling is carried out in the same manner as in the later-described third method.

Examples of the enzymes include cellulase, protease, β-1,3-glucanase and chitinase. Preferably used are enzymes containing β-1,3-glucanase (mycelial cell wall lytic enzyme) as a main component (not less than 50.0 w/w %, preferably 50.0 to 90.0 w/w %, in all the enzymes used). Particularly preferably used are enzymes containing β-1,3-glucanase as a main component and further containing chitinase and cellulase. In the invention, these enzymes can be used singly, or they can be used in combination of two or more kinds as described above.

The enzymes containing β-1,3-glucanase as a main component and further containing chitinase and cellulase are commercially available, for example, under the trade name of "Fanselase" from Yakult K.K. This Fanselase is an active enzyme produced from one strain of *Trichoderma viride,* and contains chitinase, cellulase, etc. in addition to β-1,3-glucanase as a main component. The Fanselase is able to lyse (decompose) cell walls of mushrooms to produce cytolysis products and to adjust protoplast (see: "On The New Cell Wall Lytic Enzymes" by Shinichiro Shimada, New Food Industry, Vol. 28, No. 8 (1986)).

The amount of the enzyme to be added depends on the kind of the enzyme, kind of the mycelium, etc., and it cannot be determined unconditionally. However, the enzyme is used in an amount of usually 0.01 to 1.0 g, preferably 0.3 to 0.5 g, based on 1 kg of the bagasse culture medium given after the squeezing. Particularly in case of Fanselase, it is used in an amount of usually 0.05 to 0.9 g, preferably 0.2 to 0.3 g, based on 1 kg of the bagasse culture medium. The water used herein is preferably one not containing ions such as metallic ions, and it is used in an amount of 0.5 to 1.5 kg, preferably 0.7 to 1.0 kg, based on 1 kg of the bagasse culture medium. In the invention, pH of the water does not always need to be adjusted, but it may be adjusted, if desired. In case of Fanselase, for example, pH of the water is desirably adjusted to 4.0 to 7.0, preferably 5.0 to 6.0. In case of Fanselase, the temperature of the enzyme treatment is preferably 40 to 55° C.

Inactivation of enzyme and sterilization by heating

In the present invention, the cell wall lysis product-containing liquid (ii) obtained by the above enzyme treatment, preferably a separate liquid (iii) obtained by further subjecting the cell wall lysis product-containing liquid (ii) to solid-liquid separation, is then heated up to a temperature of 95° C., preferably 70 to 90° C., to inactivate the above-mentioned enzyme and other enzymes originally contained in the bagasse and to perform sterilization. By virtue of heating at this temperature, the cell wall lysis product-containing liquid (ii) (particularly β-glucan and the like contained therein) or the separate liquid (iii) can be prevented from being denatured.

Solid-liquid separation

After the cell wall lysis product-containing liquid (ii) is heated to inactivate the enzymes and perform sterilization, the liquid (ii) may be subjected to solid-liquid separation, or after the cell wall lysis product-containing liquid is subjected to solid-liquid separation (to obtain particularly β-glucan and the like), the resulting separate liquid (secondary extract) may be heated in the same manner as described above to inactivate the enzyme and perform sterilization. For the solid-liquid separation, various means such as squeezing under the same conditions as above, centrifugal separation and filtration are employable.

The separate liquid obtained as above is milk-brown and sometimes contains fine suspended matter. The fine suspended matter is composed of culture medium decomposition products and solidified proteins and starch given by the enzyme reaction and heating. The fine suspended matter can be separated by allowing the separate liquid to stand so as to precipitate it or by filtering the liquid through a fine mesh filter cloth.

If desired, the separate liquid (suspension) thus obtained is made clearer by means of, for example, celite or a membrane filter.

In the separate liquid (extract from the solid component (i-a)), cell wall decomposition products such as β-glucan, chitin and glucose, which are obtained by decomposition of cell walls of the basidiomycetes, are contained in high concentrations, and this separate liquid shows particularly excellent antitumor effects.

In the present invention, the cell wall lysis product-containing liquid (ii) (preferably the separate liquid (iii) obtained by solid-liquid separation thereof) and the squeeze liquid (i) obtained in the previous squeezing step may be heated together under the above-mentioned conditions to perform inactivation of enzyme and sterilization.

If the cell wall lysis product-containing liquid (ii) (preferably the separate liquid (iii)) and the squeeze liquid (i) are heated together to perform inactivation of enzyme and sterilization, the number of times of the heat sterilizing operation can be decreased as compared with the case where the heat sterilizing operation of the squeeze liquid (i) obtained by the squeezing step and the heat sterilizing operation of the cell wall lysis product-containing liquid (ii) (or the separate liquid (iii)) are carried out separately.

In the present invention, the separate liquid obtained after the enzyme inactivation and sterilization may be acted on by protein decomposition enzymes such as protease to produce amino acids.

Third Method

Next, the third method for extracting useful ingredients from a mycelium-containing culture medium according to the invention is described.

In the third method of the invention, "a mycelium-containing solid culture medium" is employed. This mycelium-containing solid culture medium is the same as that described above and is obtained by inoculating basidiomycetes in a solid culture medium containing bagasse as a substrate and proliferating mycelium. In the third method, this mycelium-containing solid culture medium is disentangled, then the disentangled solid culture medium is contacted with an enzyme liquid (a) containing β-1,3-glucanase at a temperature of 30 to 60° C. for 1 to 65 minutes to lyse mycelial cell walls, and the resulting cell wall lysis product-containing liquid is heated up to a temperature of 95° C. to inactivate the enzyme and perform sterilization.

Each step of the third extraction method is described below in more detail, mainly making reference to the differences from the first extraction method.

Disentangling

In the present invention, the proliferated basidiomycetous mycelium spreads thoroughly in the culture medium. Then, immediately before or after fructification, the bagasse culture medium containing mycelium (sometimes referred to as "bagasse culture medium block" or "solid culture medium") is disentangled.

The mycelium-containing bagasse culture medium, particularly cellulose thereof, is disentangled so that the amount of 12-mesh passing disentangled culture medium becomes not more than 30 w/w %. In order to obtain more than 30 w/w % of the 12-mesh passing culture medium, a special crusher or other special means is necessary for disentangling of the bagasse cellulose, and therefore the amount of more than 30 w/w % is undesirable. In other words, when the bagasse culture medium is disentangled without using any special crusher, the amount of the 12-mesh passing culture medium becomes not more than 30 w/w %.

The disentangling of the bagasse culture medium is preferably carried out immediately before fructification.

Mycelial cytolysis

The disentangled solid culture medium is then contacted with an enzyme liquid (a) containing β-1,3-glucanase at a temperature of 30 to 60° C., preferably 35 to 55° C., for 1 to 65 minutes, preferably 10 to 60 minutes, to lyse mycelial cell walls.

If the solid culture medium and the enzyme liquid (a) are contacted at the above temperature for the above period of time, not only the enzyme (β-1,3-glucanase) but also enzymes derived from the mycelium can be utilized for lysing the cell walls, and progress of protoplast destruction as cytotoxicity is restrained. In the resulting extract, β-glucan having antitumor effects is contained in a high concentration. Moreover, cytokinin-like substances having a function of imparting immunity and a hormonic action on plants are contained in high concentrations together with glucose which is a metabolite of the mycelium, and these components are well-balanced in the extract.

The preferable temperature of the enzyme treatment varies depending on the kind of the mycelium inoculated, etc., and it cannot be determined unconditionally. In general, however, with increase of the temperature of the enzyme treatment within the above-mentioned range, the enzyme activity tends to lower, and the time required for treating the enzyme tends to be prolonged.

For contacting the disentangled solid culture medium with the enzyme liquid (a) to lyse the mycelial cell walls, various means can be utilized. For example, the whole culture medium is immersed in the enzyme liquid (a) in an amount large enough for immersing it at the same time (at once), or the enzyme liquid (a) is sprinkled on the solid culture medium, or the solid culture medium is introduced into the enzyme liquid (a) in an amount smaller than the above, followed by stirring or shaking. That is, there is no specific limitation on the contact means, as far as the solid culture medium is substantially contacted with the enzyme liquid (a) at the above temperature for the above period of time.

As the enzyme liquid (a) containing β-1,3-glucanase, a liquid containing water as its dispersing medium and containing enzymes including β-1,3-glucanase as its disperse phase is preferable. It is desirable that the β-1,3-glucanase is contained in an amount of not less than 50 w/w %, preferably 50 to 90 w/w %, in all the enzymes used.

In the enzyme liquid (a), enzymes such as chitinase, cellulase and protease may further be contained in addition to the β-1,3-glucanase. In the present invention, the enzymes (A) including β-1,3-glucanase are contained in the enzyme liquid (a) in the total amount of generally 0.5 to 10 w/w %, preferably 1 to 5 w/w %.

When the enzymes (A) containing β-1,3-glucanase as the main component, preferably further containing chitinase, cellulase and protease is used, the mycelial cell walls can be lysed (decomposed) for a short period of time with no need to pulverize the culture medium. Further, the extraction from the unpulverized culture medium can be made for a short period of time. Therefore, there is no need to carry out plural times of heating operations for enzyme inactivation and sterilization, and the heating operation is carried out once in the final extraction step.

The amount of the enzyme liquid (a) varies depending on the kind of the mycelium used, contact means of the culture medium with the enzyme liquid (a), concentration of the enzyme liquid (a), etc., and it cannot be determined unconditionally. However, when the culture medium is immersed in the enzyme liquid (a), the enzyme liquid (a) is used in such an amount that the total amount of the enzymes would be usually 0.1 to 1 g, preferably 0.3 to 0.5 g, based on 1 kg of the bagasse culture medium. In other words, the enzyme liquid (a) having a concentration of 0.01 to 0.1 w/w %, preferably 0.03 to 0.05 w/w %, is used in an amount of usually 100 to 2,000 ml, preferably 500 to 1,000 ml, based on 1 kg of the bagasse culture medium.

When the enzyme liquid (a) having the above concentration is used, mass production of β-glucan tends to be efficiently promoted because of the cell wall lysis. If a Fanselase-containing liquid having a higher concentration (e.g., 2 to 3%) than the above is used, the cell walls are completely lysed under the above-mentioned temperature and time conditions, so that mass production of β-glucan is hardly made.

The water contained in the enzyme liquid (a) is preferably one not containing ions such as metallic ions. The water is used in an amount of 100 to 2,000 g, preferably 500 to 1,000 g, based on 1 kg of the bagasse culture medium. In the invention, pH of the enzyme liquid (a) does not always need to be adjusted, but it may be adjusted, if desired. In this case, its pH is adjusted to usually 4.0 to 7.0, preferably 5.0 to 6.0.

Inactivation of enzyme and sterilization by heating

The cytolysis product-containing liquid obtained by the enzyme treatment, preferably a separate liquid obtained by further subjecting the cytolysis product-containing liquid to solid-liquid separation as previously described, is then heated in the same manner as described above to inactivate the enzyme and perform sterilization.

Solid-liquid separation

After the cell wall lysis product-containing liquid is heated to inactivate the enzyme and perform sterilization, the liquid may be subjected to solid-liquid separation, or after the cell wall lysis product-containing liquid is subjected to solid-liquid separation, the resulting separate liquid may be heated in the same manner as described above to inactivate the enzyme and perform sterilization. For the solid-liquid separation, various means such as squeezing, centrifugal separation and filtration are employable. The squeezing can be carried out in the same manner as described above (manner used to squeeze the mycelium-containing bagasse culture medium to separate it into the squeeze liquid (extract) (i) and the mycelium-containing solid component (i-a)).

In the extract (squeeze liquid) obtained above, β-glucan, proteins, various amino acids, vitamins, etc. are contained in large amounts. Similarly to the aforesaid first method of the invention, fine suspended matter sometimes remains in the extract. The fine suspended matter can be separated and removed in the same manner as described above.

If desired, the separate liquid thus obtained is made clearer by means of, for example, celite.

In the present invention, the separate liquid obtained after the enzyme inactivation and sterilization may be acted on by protein decomposition enzymes such as protease to produce amino acids.

In the separate liquid, cytokinin-like substances having a function of imparting immunity and a hormonic action on plants are contained in high concentrations together with β-glucan (which is a cell wall decomposition product obtained when the cell walls of the basidiomycetes are lysed to produce protoplast, and has high antitumor effects) and glucose (metabolite of the mycelium), and these components are well-balanced in the liquid. Moreover, this separate liquid is generally clear brown, so that application of the liquid to tonic drinks, plant hormone drugs and cosmetic materials can be expected.

According to the first to third methods of the invention for extracting useful ingredients from a mycelium-containing culture medium, useful ingredients of the basidiomycetous mycelia and the bagasse culture media can be obtained in high yields for a short period of time.

Especially by the use of the first and second methods, there can be obtained a mycelium cell wall lysis product-containing liquid (ii) (extract) which contains β-glucan of high antitumor effects in high concentration and shows particularly excellent antitumor effects. In addition to the extract (ii), a squeeze liquid (i) can be also obtained. In the squeeze liquid (i), cytokinin-like substances having a function of imparting immunity and a hormonic action on plants are contained in high concentrations along with glucose which is a metabolite of the mycelium. Moreover, the squeeze liquid (i) is generally clear, so that application of the liquid to tonic drinks, plant hormone drugs and cosmetic materials can be expected. It is also possible to apply a mixture of the squeeze liquid (i) and the mycelium cell wall lysis product-containing liquid (ii) to the above uses.

By the use of the third method, there can be obtained a cell wall lysis product-containing liquid (extract of useful ingredient) in which β-glucan and cytokinin-like substances are contained in high concentrations together with glucose and these components are well-balanced. Moreover, this extract is generally clear, so that application of the extract to tonic drinks, plant hormone drugs and cosmetic materials can be expected, similarly to the squeeze liquid (i) and the mycelium cell wall lysis product-containing liquid (ii) obtained by the first and second methods.

The present invention will be further described with reference to the following examples, but it should be construed that the invention is in no way limited to those examples.

EXAMPLE 1

Pure water was moderately added to a solid culture medium composed of 90 parts by weight of bagasse and 10 parts by weight of rice bran. Then, *Lentinus edodes* fungus was inoculated in the solid culture medium. The thus treated culture medium was allowed to stand in a culture room having been adjusted in the temperature and humidity, to proliferate *Lentinus edodes* mycelium. After the proliferated mycelium spread in the solid culture medium, the solid culture medium (a) containing proliferated mycelium was squeezed (pressed) by means of a hydraulic squeezing machine (type: KS-2, available from Komagata Kikai Seisakusho, Inc.) at a gauge pressure of 85 kg/cm$^2$ for 5 minutes and then further squeezed at a gauge pressure of 175 kg/cm$^2$ for 5 minutes (first extraction).

As a result, 0.55 kg of a mycelium-containing solid component (i-a) and 440 ml of a clear squeeze liquid (i) (primary extract, Brix concentration: 8.0%) were obtained based on 1 kg of the proliferated mycelium-containing solid culture medium (a).

Separately, to the mycelium-containing solid component (i-a) were added 1 liter of water and 0.2 g of a cell wall lytic enzyme, "Fanselase" (available from Yakult K.K.), based on 1 kg of the solid component (i-a), to give a bagasse-containing mixture. The bagasse-containing mixture was stirred for 1 hour by means of a stirring machine while maintaining the mixture at 40° C., to lyse the mycelial cell walls.

Then, the resulting enzyme-treated liquid (cell wall lysis product-containing liquid (ii)) was subjected to solid-liquid separation by means of a squeezing machine, to obtain 970 ml of an enzyme-treated extract (A-1) based on 1 kg of the mycelium-containing solid component (i-a).

Subsequently, the enzyme-treated extract was heated to 90° C. and allowed to stand for 30 minutes at this temperature. By virtue of heating to 90° C., the enzyme was inactivated and sterilization was performed.

The resulting sterilized extract was filtered through a 60-mesh filter cloth, to obtain 950 ml of an extract containing fine suspended matters (secondary extract, Brix concentration: 2.5 w/w %) based on 1 kg of the proliferated mycelium-containing solid culture medium (a).

In each of the primary extract and the secondary extract, proteins, saccharides, minerals, β-glucan, etc. were contained together with water, and the contents thereof are set forth in Table 1.

As the solid residue, a sufficiently finely ground product was obtained. After drying, the ground product was used as feed of livestock such as cows.

TABLE 1

(*Lentinus edodes* mycelium)

|  | Primary Extract (%) | Secondary Extract (%) |
|---|---|---|
| Proteins | 21.5 | 33.7 |
| Saccharides | 42 | 44.2 |
| Ash content | 26.1 | 15.4 |
| β-Glucan | 0.5 | 2.5 |

From Table 1, it has been confirmed that large amounts of active ingredients are contained in the two kinds of the extracts obtained in the method of the invention and the primary extract is different from the secondary extract in the content of β-glucan.

EXAMPLE 2

(Method including disentangling and grinding by means of a speed change gear pump)

Pure water was moderately added to a solid culture medium composed of 90 parts by weight of bagasse and 10 parts by weight of rice bran. Then, *Flammulina velutipes* fungus was inoculated in the solid culture medium. The thus treated culture medium was allowed to stand in a culture room having been adjusted in the temperature and humidity, to proliferate *Flammulina velutipes* mycelium. After the proliferated mycelium spread in the solid culture medium, the solid culture medium (a) containing proliferated mycelium was squeezed (pressed) by means of a hydraulic squeezing machine (type: KS-2, available from Komagata Kikai Seisakusho, Inc.) at a gauge pressure of 85 kg/cm$^2$ for 5 minutes and then further squeezed at a gauge pressure of 175 kg/cm$^2$ for 5 minutes (first extraction).

As a result, 0.65 kg of a mycelium-containing solid component (i-a) and 350 ml of a clear squeeze liquid (primary extract, Brix concentration: 5.7%) were obtained based on 1 kg of the proliferated mycelium-containing solid culture medium (a).

Separately, the mycelium-containing solid component (i-a) was disentangled so that the amount of the 12-mesh passing solid component became not more than 24 w/w %. To 1.0 kg of the disentangled culture medium were added 1.0 liter of pure water and 0.2 g of purified cellulase as an enzyme to give a bagasse-containing mixture.

Then, while the culture medium-containing mixture kept at 40° C. was circulated by means of a speed change gear pump, the solid culture medium was crushed and ground at the gear part of the pump for 150 minutes so that the amount of the 12-mesh passing bagasse fibers became about 80 w/w %.

Subsequently, the bagasse-containing mixture was heated to 90° C. and allowed to stand for 30 minutes at this temperature. By virtue of heating to 90° C., the enzyme was inactivated and sterilization was performed.

The resulting culture medium-containing mixture was filtered through a 60-mesh filter cloth, to obtain 950 ml of an extract containing fine suspended matters (secondary extract, Brix concentration: 1.9 w/w %) based on 1 kg of the proliferated mycelium-containing solid culture medium (a).

In each of the primary extract and the secondary extract, proteins, saccharides, minerals, β-glucan, etc. were contained along with water, and the contents thereof are set forth in Table 2.

As the solid residue, a sufficiently finely ground product was obtained. After drying, this ground product was used as feed of livestock such as cows.

TABLE 2

(*Flammulina velutipes* mycelium)

|  | Primary Extract (%) | Secondary Extract (%) |
|---|---|---|
| Proteins | 24.1 | 37.2 |
| Saccharides | 40.1 | 42.2 |
| Ash content | 24.4 | 14.9 |
| β-Glucan | 0.4 | 2.1 |

From Table 2, it has been confirmed that large amounts of active ingredients are contained in the two kinds of the extracts obtained in the method of the invention and the primary extract is different from the secondary extract in the content of β-glucan.

EXAMPLE 3

A primary extract was obtained in the same manner as in Example 1, except that *Ganoderuma lucidium* fungus was used in place of *Lentinus edodes* fungus.

As a result, 0.6 kg of a mycelium-containing solid component (i-a) and 400 ml of a clear squeeze liquid (i) (primary extract, Brix concentration: 7.6%) were obtained based on 1 kg of the proliferated mycelium-containing solid culture medium (a).

Separately, to the mycelium-containing solid component (i-a) were added 1 liter of water and 0.15 g of a cell wall lytic enzyme, "Fanselase" (available from Yakult K.K.), based on 1 kg of the solid component (i-a), to give a bagasse-containing mixture. The bagasse-containing mixture was stirred for 1 hour by means of a stirring machine while maintaining the mixture at 40° C., to lyse the mycelial cell walls.

Then, the resulting enzyme-treated mixture (cell wall lysis product-containing liquid (ii)) was subjected to solid-liquid separation by means of a squeezing machine, to obtain 950 ml of an enzyme-treated extract (A-1) based on 1 kg of the mycelium-containing solid component (i-a).

Subsequently, the enzyme-treated extract was heated to 90° C. and allowed to stand for 30 minutes at this temperature. By virtue of heating to 90° C., the enzyme was inactivated and sterilization was performed.

The resulting sterilized extract was filtered through a 60-mesh filter cloth to obtain 900 ml of an extract containing fine suspended matters (secondary extract, Brix concentration: 3.2 w/w %) based on 1 kg of the proliferated mycelium-containing solid culture medium (a).

In each of the primary extract and the secondary extract, proteins, saccharides, minerals, $\beta$-glucan, etc. were contained along with water, and the contents thereof are set forth in Table 3.

As the solid residue, a sufficiently finely ground product was obtained. After drying, this ground product was used as feed of livestock such as cows.

TABLE 3

(Ganoderuma lucidium mycelium)

|  | Primary Extract (%) | Secondary Extract (%) |
| --- | --- | --- |
| Proteins | 19.8 | 26.9 |
| Saccharides | 40.7 | 37.3 |
| Ash content | 38.8 | 19.9 |
| $\beta$-Glucan | 0.5 | 1.9 |

COMPARATIVE EXAMPLE 1

(Enzyme grinding method)

1 kg of the same solid culture medium as used in Example 1 was disentangled. To the disentangled culture medium was added 3 liters of an enzyme liquid containing cellulase in a concentration of 0.05% and protease in a concentration of 0.05%. Then, the resulting mixture was maintained at 40° C. and circulated with stirring and grinding by means of a gear pump, to perform reaction for 1 hour. After the reaction was completed, the mixture was heated to 70° C. and maintained at this temperature for 30 minutes to inactivate the enzymes. Then, the mixture was subjected to solid-liquid separation by means of centrifugal separation to obtain about 2,800 ml of an extract having a Brix concentration of 2.0 w/w %.

COMPARATIVE EXAMPLE 2

(Stationary circulating method)

1 kg of the same solid culture medium as used in Example 1 was crushed and wrapped in a filter cloth. To the culture medium was added 5 liters of water, and the thus treated culture medium was maintained at 50° C. The liquid was circulated by means of a pump. Then, the culture medium and the liquid were allowed to stand for 15 hours and subjected to solid-liquid separation to obtain about 4,400 ml of an extract having a Brix concentration of 0.7 w/w %.

EXAMPLE 4

Pure water was moderately added to a solid culture medium composed of 90 parts by weight of bagasse and 10 parts by weight of rice bran. Then, *Lentiuns edodes* fungus was inoculated in the solid culture medium. The thus treated culture medium was allowed to stand in a culture room having been adjusted in the temperature and humidity, to proliferate *Lentinus edodes* mycelium. After the mycelium spread in the solid culture medium, 1 kg of the solid culture medium (i) containing proliferated mycelium was immersed in 1 liter of an enzyme liquid (a) containing $\beta$-1,3-glucanase as a main component and further containing chitinase and cellulase (concentration of all the enzymes in the enzyme liquid: 0.04 w/w %, content of $\beta$-1,3-glucanase (main component) in all the enzymes: 50 w/w %), then maintained at 40° C. and stirred for 60 minutes by means of a stirring machine, to lyse the mycelial cell walls.

Then, the resulting enzyme-treated mixture (cell wall lysis product-containing liquid) was subjected to solid-liquid separation by means of a squeezing machine (solid-liquid separator), to obtain 1,500 ml of an enzyme-treated extract (A-1).

Subsequently, the enzyme-treated extract was heated to 90° C. and allowed to stand for 30 minutes at this temperature. By virtue of heating to 90° C., the enzymes were inactivated and sterilization was performed.

The resulting sterilized extract was filtered through a 60-mesh filter cloth to obtain 1,400 ml of an extract containing fine suspended matter (Brix concentration: 4.0 w/w %) based on 1 kg of the proliferated mycelium-containing solid culture medium (i).

In the extract, proteins (including amino acid as a protein partial-decomposition product), saccharides, minerals, $\beta$-glucan, etc. were contained along with water. Further, metabolites of the mycelium and the mycelial cell wall decomposition products (e.g., $\beta$-glucan) were contained with a good balance.

The contents of the active ingredients in the extract are set forth in Table 4.

As the solid residue, a sufficiently finely ground product was obtained. After drying, the ground product was used as feed of livestock such as cows.

EXAMPLE 5

Culturing of mycelium was carried out in the same manner as in Example 4, except that *Flammulina velutipes* fungus was used in place of *Lentinus edodes* fungus. Then, the mycelial cell walls were dissolved in the same manner as in Example 4 by the use of a stirring machine.

Subsequently, the resulting enzyme-treated mixture was subjected to solid-liquid separation to obtain 1,300 ml of an enzyme-treated extract (A-1).

The enzyme-treated extract was then heated to perform inactivation of enzymes and sterilization. The resulting sterilized extract was filtered in the same manner as in Example 4, to obtain 1,150 ml of an extract containing fine suspended matter (Brix concentration: 3.3 w/w %) based on 1 kg of the proliferated mycelium-containing solid culture medium (i).

In the extract, metabolites of the mycelium and mycelial cell wall decomposition products (e.g., β-glucan) were contained with a good balance.

The contents of the active ingredients in the extract are set forth in Table 4.

The solid residue was used as feed of livestock in the same manner as in Example 4.

EXAMPLE 6

Culturing of mycelium was carried out in the same manner as in Example 4, except that *Ganoderuma lucidium* fungus was used in place of *Lentinus edodes* fungus. Then, the mycelial cell walls were dissolved in the same manner as in Example 4 by the use of a stirring machine.

Subsequently, the resulting enzyme-treated mixture was subjected to solid-liquid separation to obtain 1,450 ml of an enzyme-treated extract (A-1).

The enzyme-treated extract was then heated to perform inactivation of enzymes and sterilization. The resulting sterilized extract was filtered in the same manner as in Example 4, to obtain 1,300 ml of an extract containing fine suspended matter (Brix concentration: 4.5 w/w %) based on 1 kg of the proliferated mycelium-containing solid culture medium (i).

In the extract, metabolites of the mycelium and mycelial cell wall decomposition products (e.g., β-glucan) were contained with a good balance.

The contents of the active ingredients in the extract are set forth in Table 4.

The solid residue was used as feed of livestock in the same manner as in Example 4.

TABLE 4

|  | Ex. 4 (%) | Ex. 5 (%) | Ex. 6 (%) |
|---|---|---|---|
| Kind of mycelium | Lentinus edodes mycelium | Flammulina velutipes mycelium | Ganoderuma lucidium mycelium |
| Proteins | 27.6 | 30.7 | 23.4 |
| (Amino acid) | (20.8) | (24.8) | (14.9) |
| Saccharides | 43.1 | 41.2 | 39.0 |
| Ash content | 20.8 | 19.7 | 29.4 |
| β-Glucan | 1.5 | 1.3 | 1.2 |

COMPARATIVE EXAMPLE 3
(Enzyme grinding method)

1 kg of the same solid culture medium as used in Example 4 was disentangled. To the disentangled culture medium was added 3 liters of an enzyme liquid containing cellulase in a concentration of 0.05% and protease in a concentration of 0.05%. Then, the resulting mixture was maintained at 40° C. and circulated with stirring and grinding by means of a gear pump, to perform reaction for 1 hour. After the reaction was completed, the mixture was heated to 70° C. and maintained at this temperature for 30 minutes to inactivate the enzymes. Then, the mixture was subjected to solid-liquid separation by means of centrifugal separation to obtain about 2,800 ml of an extract having a Brix concentration of 2.0 w/w %.

COMPARATIVE EXAMPLE 4
(Stationary circulating method)

1 kg of the same solid culture medium as used in Example 4 was crushed and wrapped in a filter cloth. To the culture medium was added 5 liters of water, and the thus treated culture medium was maintained at 50° C. The liquid was circulated by means of a pump. Then, the culture medium and the liquid were allowed to stand for 15 hours and subjected to solid-liquid separation, to obtain about 4,400 ml of an extract having a Brix concentration of 0.7 w/w %.

What is claimed is:

1. A method for obtaining an extract from a mycelium-containing culture medium, comprising the steps of:

inoculating basidiomycetes in a solid culture medium containing bagasse as a substrate;

proliferating mycelium of the basidiomycetes;

applying pressure to the solid culture medium containing proliferated mycelium to obtain a squeeze liquid therefrom;

separating a mycelium-containing solid residue from the squeeze liquid;

adding water and an enzyme containing β-1,3-glucanase as a main ingredient together with at least one enzyme selected from the group consisting of protease, chitinase and cellulase to the mycelium-containing solid residue to produce a mixture;

stirring the mixture while maintaining the mixture at 30 to 60° C. to lyse mycelial cell walls; and heating the resulting cell wall lysis product-containing liquid up to a temperature of 95° C. to inactivate the enzymes and perform sterilization, thereby producing an extract of the mycelium-containing culture medium.

2. A method for obtaining an extract from a mycelium-containing culture medium, comprising the steps of:

inoculating basidiomycetes in a solid culture medium containing bagasse as a substrate;

proliferating mycelium of the basidiomycetes;

applying pressure to the solid culture medium containing proliferated mycelium to obtain a squeeze liquid therefrom;

separating a mycelium-containing solid residue from the squeeze liquid;

disentangling the mycelium-containing solid residue;

adding water and an enzyme containing β-1,3-glucanase as a main ingredient together with at least one enzyme selected from the group consisting of protease, chitinase and cellulase to the disentangled solid residue to produce a mixture;

crushing and grinding the solid residue while maintaining the mixture at 30 to 60° C. to lyse mycelial cell walls; and heating the resulting cell wall lysis product-containing liquid up to a temperature of 95° C. to inactivate the enzymes and perform sterilization, thereby producing an extract of the mycelium-containing culture medium.

3. The method as claimed in claim 2, further comprising stirring the mixture while maintaining the enzymatic mixture at 30 to 60° C. to lyse mycelial cell walls.

4. A method for obtaining an extract containing a cell wall lysis product-containing liquid from a mycelium-containing culture medium, comprising the steps of:

inoculating basidiomycetes in a solid culture medium containing bagasse as a substrate;

proliferating mycelium of the basidiomycetes;

disentangling the proliferated mycelium contained in the solid culture medium;

contacting the solid culture medium containing the disentangled mycelium with a liquid containing β-1,3-glucanase as a main ingredient together with at least one enzyme selected from the group consisting of protease, chitinase and cellulase at a temperature of 30 to 60° C. for 1 to 65 minutes to lyse mycelial cell walls to obtain a cell wall lysis product-containing liquid; and heating the cell wall lysis product-containing liquid up to a temperature of 95° C. to inactivate the enzymes and perform sterilization, thereby producing an extract of the mycelium-containing culture medium.

5. The method as claimed in claim 4, wherein 100 to 2,000 ml of the β-1,3-glucanase-containing liquid having a concentration of 0.01 to 0.1 w/w % β-1,3-glucanase is allowed to act on 1 kg of the solid culture medium.

6. The method as claimed in claim 4, wherein contacting the solid culture medium containing the disentangled mycelium with the β-1,3-glucanase-containing liquid is carried out by immersing the solid culture medium in the β-1,3-glucanase-containing liquid.

7. The method as claimed in claim 4, further comprising separating the cell wall lysis product-containing liquid from the solid culture medium and heating the cell wall lysis product-containing liquid up to a temperature of 95° C. to inactivate the enzymes and perform sterilization.

* * * * *

UNITED STATES PATENT AND TRADEMARK OFFICE
CERTIFICATE OF CORRECTION

PATENT NO.   : 6,090,615
DATED        : July 18, 2000
INVENTOR(S)  : Hitoshi Nagaoka It is certified that error appears in the above-identified patent and that said Letters Patent is hereby corrected as shown below:

Title Page, [57] ABSTRACT, Line 11 "60°0 C" should read --60° C--.

Column 15 Table 4 under Example 6 "39.()" should read --39.0--.

Signed and Sealed this

Seventeenth Day of April, 2001

*Attest:*

NICHOLAS P. GODICI

*Attesting Officer*    Acting Director of the United States Patent and Trademark Office